United States Patent [19]

Seprodi et al.

[11] Patent Number: 4,751,215

[45] Date of Patent: Jun. 14, 1988

[54] PROCESS FOR INCREASING THE SEXUAL ACTIVITY OF BIRDS AND USEFUL DOMESTIC MAMMALS AND FOR PREPARING SPERMATOZOA SUITABLE TO THEIR PROPAGATION

[75] Inventors: Janos Seprodi, Budapest; Zsolt Vadasz, Tardosbanya; Peter Peczely, Gyomro; Istvan Teplan, Budapest; Judit Erchegyi, Budapest; Tibor Muray, Budapest; Istvan Gyorvari, Nadudvar, all of Hungary

[73] Assignee: INNOFINANCE Altalanos Innovacios Penzintezet, Budapest, Hungary

[21] Appl. No.: 852,217

[22] Filed: Apr. 15, 1986

[30] Foreign Application Priority Data

Apr. 16, 1985 [HU] Hungary ............................. 1405/85

[51] Int. Cl.$^4$ ............................................ A61K 37/24
[52] U.S. Cl. ...................................... 514/15; 514/800
[58] Field of Search .................................. 514/15, 800

[56] References Cited

U.S. PATENT DOCUMENTS

| | | | |
|---|---|---|---|
| 3,914,412 | 10/1975 | Gendrich et al. | 514/15 |
| 4,008,209 | 2/1977 | Fujino et al. | 530/313 |
| 4,083,967 | 4/1978 | Beddell et al. | 514/15 |
| 4,382,922 | 5/1983 | Rivier et al. | 514/15 |

OTHER PUBLICATIONS

Miyamoto et al, *Proc. Natl. Acad. Sci. USA*, 81, 3874–78 (1984).
Dutta et al. (1985) Ann. Rep. Med. Chem. 20: 203–214.
Seprodi et al. (1986) 19th European Peptide Symposium, Posto Carras, Greece.
J. Biol. Chem. (1966) 241: 527–533.
J. Biol. Chem. (1972) 247: 977–983.
Skarin et al. (1984) Upsala J. Med. Sci. 89: 73–80.
Hoffman et al. (1982) New Engl. J. Med. 307(20): 1237–1241.
Kelnar (1983) Horm. Res. 18: 168–174.
Brook et al. (1979) Clin. Endocrinol. 11: 81–87.

*Primary Examiner*—J. R. Brown
*Assistant Examiner*—F. T. Moezie
*Attorney, Agent, or Firm*—Keil & Weinkauf

[57] ABSTRACT

The invention relates to a process for increasing the sexual activity of birds and useful domestic mammals and for preparing spermatozoa suitable to their propagation. The process of the invention comprises treating sexually mature male birds or useful domestic mammals at least twice and at most four times with 0.1 to 5 μg/kg of body weight of a compound of the general formula (I), $$\text{Glp-His-Trp-Ser-Tyr-}X_1\text{-Leu-Arg-Pro-}X_4 \qquad (I)$$

wherein $X_1$ stands for a glycyl group, a natural or synthetic aminoacid or aminoacid derivative of D configuration, an -Asp-Q group of L configuration, wherein Q is attached to the α-carbonyl moiety of the aspartyl group and represents a $C_{1-5}$ alkylamide, an arylamide, a $C_{1-4}$ alkoxy or a benzyloxy group; and $X_4$ stands for a glycylamide or a $C_{1-4}$ alkylamide group, while keeping a pause of at least 30 hours and at most 72 hours between the consecutive treatments.

The process of the invention can mainly be used in such large-scale breedings, where artificial insemination is employed but it can be used also for any domestic bird or cought wild-fowl and ornamental bird as well as useful domestic mammal under the conditions of the natural reproduction or artificial insemination.

7 Claims, 4 Drawing Sheets

PROCESS FOR INCREASING THE SEXUAL ACTIVITY OF BIRDS AND USEFUL DOMESTIC MAMMALS AND FOR PREPARING SPERMATOZOA SUITABLE TO THEIR PROPAGATION

The invention relates to an improved process for increasing the sexual activity of birds and useful domestic mammals and for preparing the spermatozoa suitable to their propagation. The process of the invention makes possible to permanently enhance the sexual activity and sperm production (spermatogenesis) of male birds and useful domestic mammals, particularly of male turkeys, ganders, cattles and rabbits.

The gonadotropic horomone-releasing hormone (GnRH), isolated the first time from swine, proved to have an identical structure with that of GnRH obtained since then from other species (man, monkey, cattle, sheep, horse, rat, hamster, etc.). The GnRH hormone is formed in the hypthalamus on the effect of nervous stimulation and gets through the blood flow to the hypophysis where the gonadotropic hormones [luteinizing hormone (LH) and follicle-stimulating hormone (FSH)] are released. By the gonadotropins, the reproduction is controlled either directly or by the release of other hormones, e.g., testoterone.

The structural analogues of the mammalian GnRH, being derivatives substituted at the 6- and 10-positions, have an increased effect of longer duration as compared to the native hormone.

The endocrine actions of GnRH were studied with male birds: on cocks [Furr et al.: J. Endocrinology 59, 495 (1973); Danse et al.: Poultry Science 56, 2016 (1977); Pethes et al.: Acta Physiologica Hung. 56, 281 (1980)]; on guinea-fowls [Mathis et al.: Poultry Science 62, 715 (1983)]; on domestic drakes and ganders [Péczely et al.: General Comparative Endrocrinology 57, 293 (1985)]; as well as on yellow hammers [Wingfield et al.: Biological Reproduction, 21, 801 (1979)].

It has been shown by experiments described in the literature that an intense LH release was evoked in male birds by GnRH or its analogues having an agonistic action. This effect reached a maximum in the 5th to 20th minutes and later in the 60th to 120th minutes. The testosterone level of the blood plasma was also raised by GnRH. However, no data concerning an increase in the sperm production have been reported so far in the literature.

A considerable part of several birds and useful domestic mammals (e.g. cattle, rabbit, turkey, goose, etc.) bred on a large scale is artificially propagated in such a way that the sperm drained from the male animals is classified according to its quality, the useful samples are diluted with a specific sperm-diluting solution, then the females are artificially inseminated by using the thus-obtained diluted sperm. The efficiency of this method extraordinarily depends on the quality (motility, viability, storability and the like) of the spermatozoa. A relatively low part of the males is suitable to afford a sperm of good quality and useful for insemination whereas an unresticted availability of the inseminating material is required for any method used on a large scale.

The invention is aimed at the elaboration of a method rendering possible the increase in the sexual activity and sperm production of male birds and useful domestic mammals.

The invention is based on the recognition that the above-mentioned object can be accomplished, i.e. the sexual activity and sperm production of male birds and useful domestic mammals can permanently be increased, by using the compounds of the general formula (I),

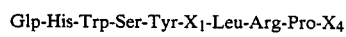

$$\text{Glp-His-Trp-Ser-Tyr-}X_1\text{-Leu-Arg-Pro-}X_4 \qquad (I)$$

wherein $X_1$ stands for a glycyl group, a natural or synthetic aminoacid or aminoacid derivative of D configuration, an -Asp-Q group of L configuration, wherein Q is attached to the α-carbonyl moiety of the aspartyl group and represents a $C_{1-5}$ alkylamide, an arylamide, a $C_{1-4}$ alkoxy or a benzyloxy group; and $X_4$ stands for a glycylamide or a $C_{1-4}$ alkylamide group.

The compounds of the general formula (I) are prepared in a manner known per se (Suisse patent specification No. 603,559; German patent specification No. 2,438,350; Hungarian patent application No. 1062/83).

Accordingly, the invention relates to a process for increasing the sexual activity of birds and useful domestic mammals as well as for preparing the spermatozoa suitable to their propagation. The process of the invention comprises treating sexually mature birds or useful domestic mammals at least twice, at most four times and preferably three times with 0.1 to 5 μg/kg of body weight, preferably with 0.5 to 1.0 μg/kg of body weight, of the compounds of general formula (I) while keeping a pause of at least 30 hours, at most 72 hours, suitably 36 to 42 hours between the consecutive treatments.

The process of the invention is suitable for treating male birds and useful domestic mammals kept and fed under natural light conditions or under artificial light prescribed in the production technology.

The GnRH analogue compound is injected intramuscularly, subcutaneously or into the blood flow. The sperm production is raised and the libido is strengthened by 30 to 120% on the effect of this treatment within 5 to 20 days, calculated from the first injection.

In case of several animal species, only the volume of the sperm is increased under effect of the treatment whereas its quality is not altered (e.g. in case of male turkeys); in case of other species, the quality of the sperm is also improved in addition to the increase in the sperm volume (e.g. in case of ganders).

In the course of time, the rise of the sexual activity achieved by the above treatment and the increase in the sperm volume are abolished, even a regression may occur. In such cases, the treatment may be repeated. It is suitable to keep an interval of 30 to 50 days between the treatments as it is possible that within this period the eventually diminishing sperm production will show a second supranormal rise.

In case of animal species where the procedure of the insemination has been elaborated (e.g. turkey, rabbit, cattle), the sexual product should be collected by using a message or an other method. In case of animal species where the method of insemination cannot be used, the efficiency of the process can be assessed on the appearance of a higher inclination to mating (higher libido) or on the higher ability of insemination.

In Table 1, the relation of the doses of the compounds of general formula (I) to the blood plasma testosterone level of the treated animals is illustrated in case of domestic cocks.

In Table 2, the influence on the sperm production of the interval kept between the consecutive treatments is shown on male turkeys.

TABLE 1

Effect of various doses of the D-Phe⁶—GnRH analogue on the blood plasma testosterone level (ng/ml) of domestic cock

| Dose μg/kg | No. of animals tested | Testosterone level of the blood plasma after minutes | | | |
|---|---|---|---|---|---|
| | | 0 | 30 | 60 | 120 |
| 0.01 | 10 | 1.7 (0.7) | 1.6 (1.3) | 1.5 (1.0) | 1.4 (0.6) |
| 0.05 | 10 | 1.4 (0.7) | 1.7 (1.2) | 1.5 (1.2) | 1.9 (0.8) |
| 0.1 | 8 | 1.0 (0.2) | 3.4 (1.9) | 2.7 (1.1) | 2.0 (0.8) |
| 0.3 | 10 | 2.1 (0.7) | 3.9 (0.6) | 4.2 (1.2) | 2.6 (0.5) |
| 0.5 | 6 | 2.5 (1.0) | 6.5 (0.5) | 5.3 (1.2) | 3.9 (1.5) |
| 1.0 | 8 | 1.5 (0.8) | 7.2 (3.5) | 7.1 (3.6) | 3.7 (1.2) |
| 3.0 | 10 | 1.9 (0.3) | 6.2 (2.4) | 5.2 (1.7) | 3.0 (1.1) |
| 5.0 | 6 | 2.1 (1.2) | 3.6 (2.4) | 2.7 (0.6) | 1.7 (0.9) |

TABLE 2

Effect of three intramuscular injections of the D-Phe⁶—GnRH analogue on the sperm production of male turkey on the 20th day following the first injection

| Interval between two consecutive treatments (hour) | No. of animals tested | Dose μg/kg | Sperm volume ml | |
|---|---|---|---|---|
| | | | on day 0 | on the 20th day |
| 24 | 50 | 1 | 0.18 (0.05) | 0.21 (0.10) |
| 48 | 50 | 1 | 0.19 (0.07) | 0.35 (0.12) |
| 72 | 50 | 1 | 0.16 (0.08) | 0.25 (0.11) |
| 144 | 50 | 1 | 0.21 (0.07) | 0.24 (0.09) |

Figure 1:
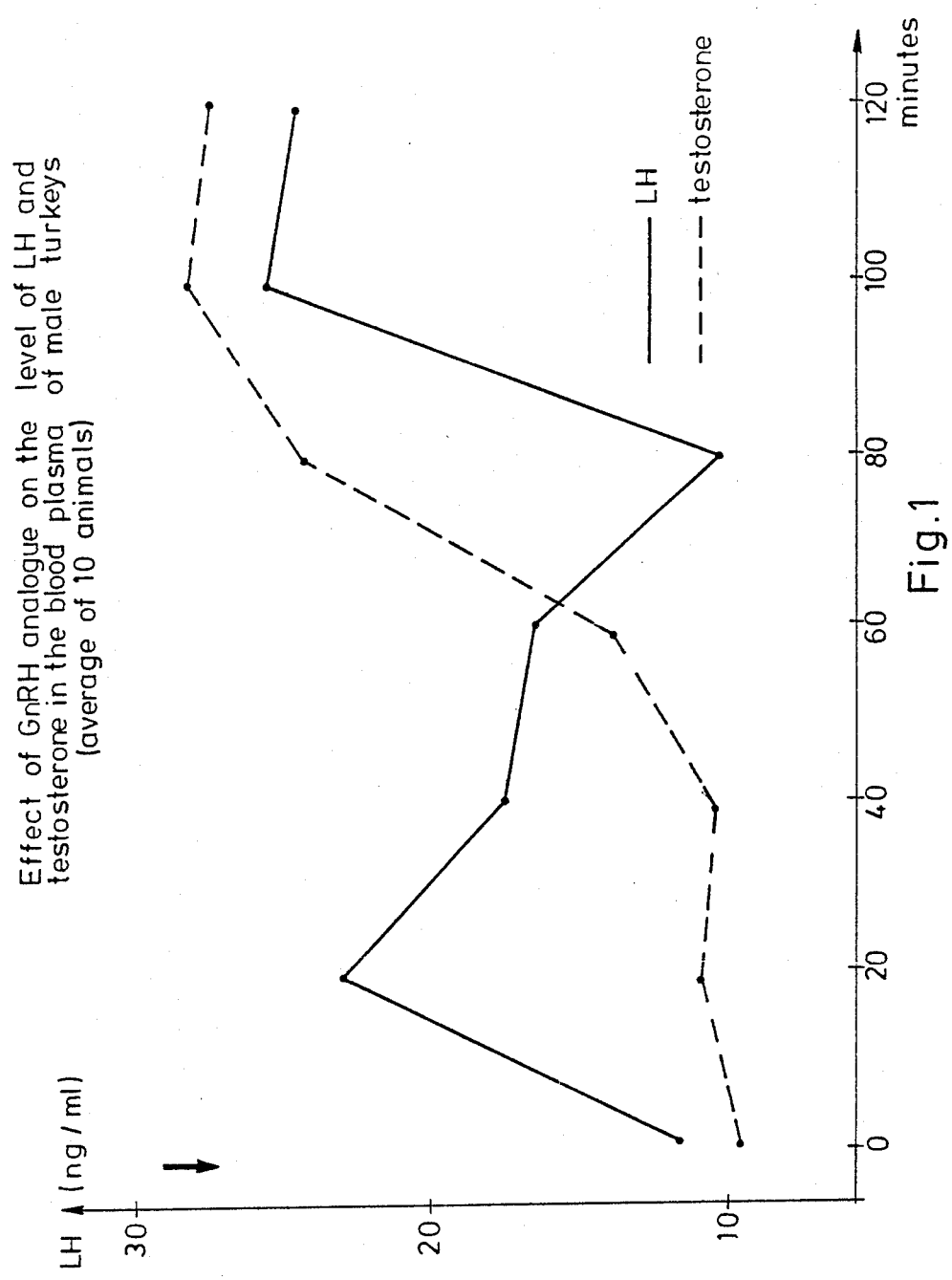
FIG. 1 shows effect of GnRH analogue on the level of LH and testosterone in the blood plasma of male turkeys (average of 10 animals).
Figure 2:
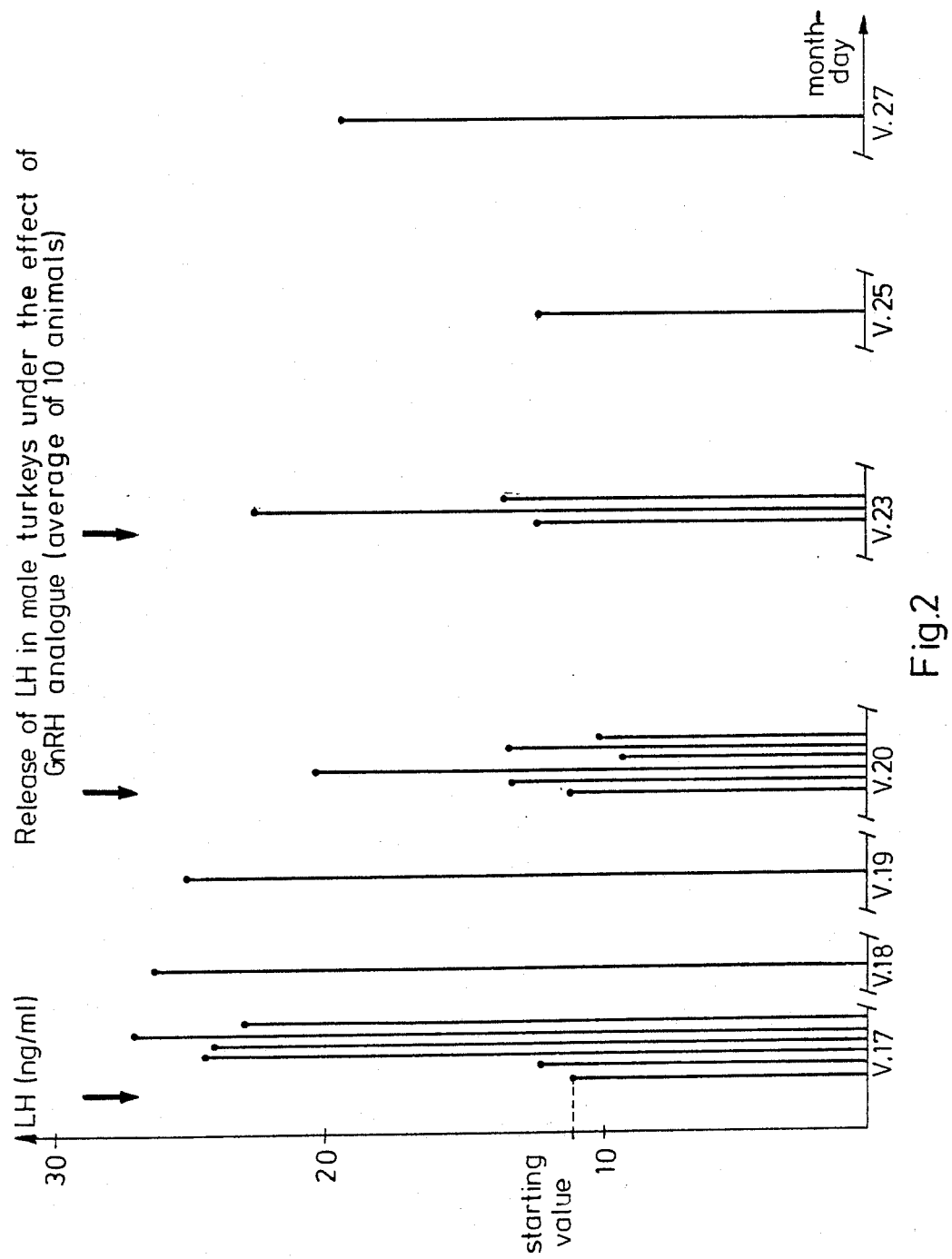
FIG. 2 shows release of LH in male Turkeys under the effect of GnRH analogue (average of 10 animals).

A characteristic two-phase response in the blood plasma LH Level of birds and useful domestic mammals is challenged by administering the GnRH analogues of the general formula (I). The first increase in the LH level appearing after the first injection (the time points of the injections are signed by vertical arrows) is followed by a slow diminution and then by a renewed rise after 100 minutes (FIG. 1). The LH concentration of the blood plasma is maintained at a high level within 3 days following the first treatment (May 17th) and decreases to the starting value only on the 3rd day (FIG. 2). After the second injection (May 20th), the LH release stops after 3 hours and the same phenomenon is observed after the third injection (May 23rd).

Figure 3:
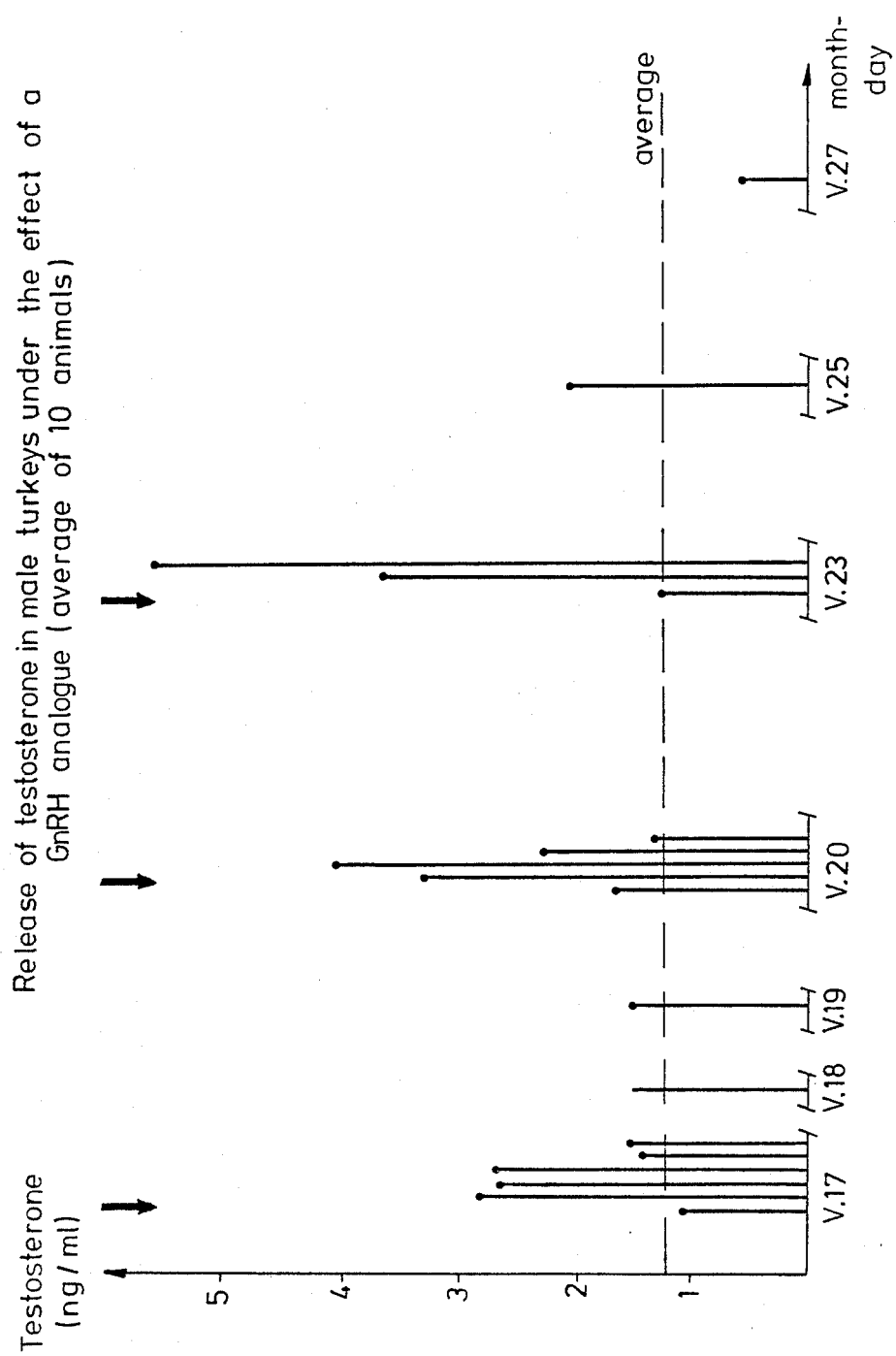
FIG. 3 shows release of testosterone in male turkeys under the effect on GnRH analogue (average of 10 animals).

The development of a permanently high LH level, following the first GnRH injection and resulting in a permanent gonadostimulation is a phenomenon not reported so far which may be one of the (essential) factors inducing the sperm production increase appearing after 2 to 3 weeks. After repeating the injections, this plateau of the LH overproduction does not develop, obviously as a consequence of the desensitizing effect of GnRH at the hypophysis level. Similarly, a characteristic phenomenon not observed hitherto consists in that the blood plasma testosterone level gives a gradually strengthening response to the consecutive injections (FIG. 3). Here, a pronounced sensitization appears at the gonadal level. The androgenic secretion-increasing gonad-sensitizing action of the repeated treatments may also be an important factor of the permanent sperm-producing effect.

The important advantages of the process of the invention are as follows:

(a) The process is useful for a permanent increase in the spermatogenesis of animals having a normal or diminished sperm production or eventually a spermatogenesis stopped for a short time, (b) The process can be utilized in such large-scale breedings (e.g. in the breeding of turkeys) where artificial insemination is used but it can be employed also for other domestical birds, caught wild-fowls and ornamental birds under the conditions of the natural reproduction or artificial insemination.

(c) A lower number of male animals has to be kept, fed and provided with veterinary hygienic care in order to assure the same or increased number of offsprings which results in the expansion and economy of the production. A higher possibility is achieved to obtain a great number of offsprings within a short period from a male which is valuable from any point of view.

The process of the invention is illustrated in detail in the following non-limiting Examples. The "μg/kg of body weight" expression is abbreviated as "μg/kg".

EXAMPLE 1

Figure 4:
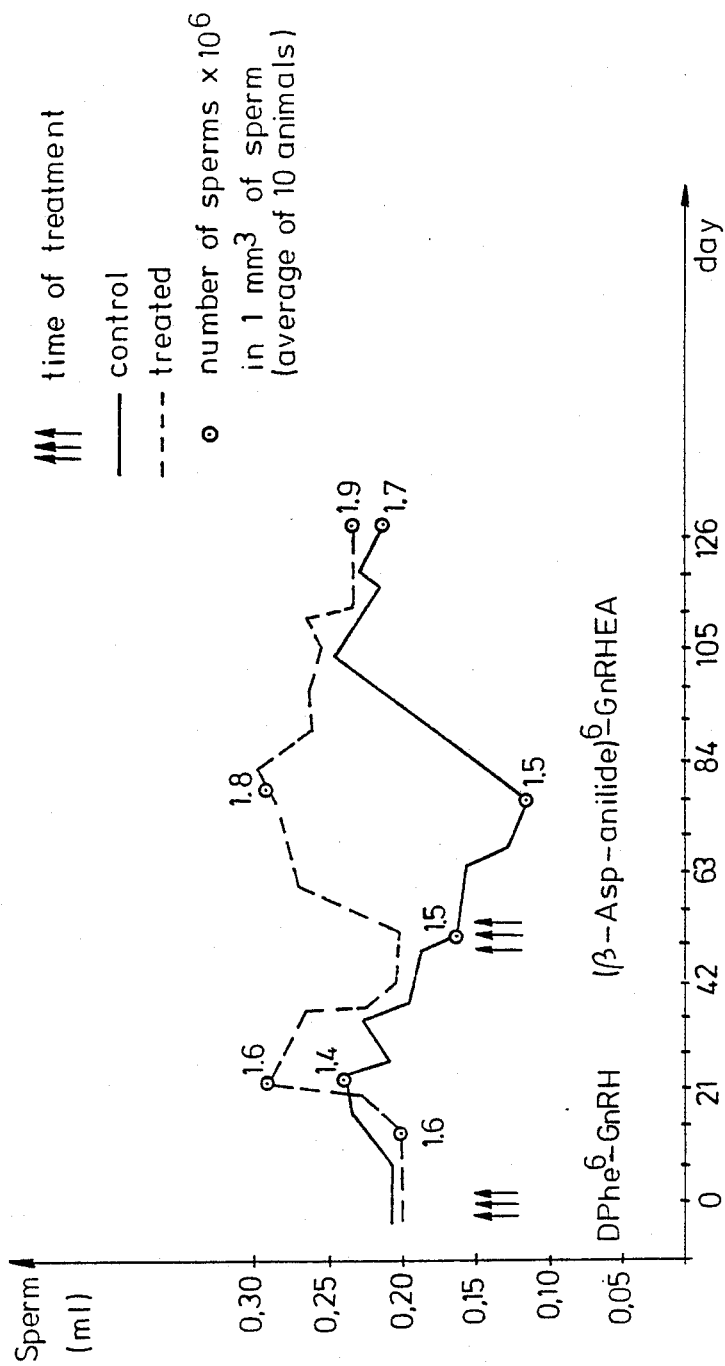
FIG. 4 shows effect of GnRH analogue on the sperm production of male turkeys.

Permanent increase in the sperm production of male turkeys bred on a large scale 0.5 μg/kg of D-Phe⁶-GnRH analogue was intramuscularly administered to sexually mature male turkeys every 2 days, altogether 3 times. On the 20th day following treatment, the sperm production reached an increase of 44% and remained at a higher level, as compared to the control, for about 1 month (FIG. 4).

One month and half after the first treatment, the same animals were similarly treated with 0.5 μg/kg of (Asp-α-diethylamide)⁶,desGly¹⁰-GnRH ethylamide analogue every 2 days, altogether 3 times. This treatment resulted in an immediate increase of 45% in the sperm production and provided a significantly higher level, as compared to the control, for about 2 months (FIG. 4). It is clearly seen on FIG. 4 that the number of the spermatozoa in unit volume also became significantly higher.

The rise of the LH level of the blood was followed by an increase in the testosterone level (Table 3).

| Sampling time | Testosterone ng/ml | |
|---|---|---|
| | Control (n = 15) | Treated (n = 15) |
| May 2 | 2.65 ± 1.05 | 2.43 ± 1.22 |
| May 23 | 2.80 ± 1.10 | 4.06 ± 1.62 |
| June 22 | 2.34 ± 0.89 | 3.25 ± 1.11 |
| July 18 | 1.76 ± 0.82 | 3.89 ± 1.34 |
| September 8 | 2.76 ± 1.18 | 2.53 ± 1.00 |

In another experiment, sexually mature male turkeys were treated with 0.5 μg/kg of (Asp-α-diethylamide)⁶,desGly¹⁰-GnRH ethylamide analogue every 3 days, altogether 3 times. This treatment procedure resulted in a rise of the sperm production, too (Table 4).

| Sampling | Sperm ml/animal | |
|---|---|---|
| time | Control (n = 15) | Treated (n = 15) |
| May 17 | 0.18 ± 0.07 | 0.20 ± 0.06 |
| May 20 | 0.20 ± 0.09 | 0.20 ± 0.09 |
| May 23 | 0.19 ± 0.09 | 0.21 ± 0.05 |
| May 30 | 0.20 ± 0.06 | 0.25 ± 0.07 |
| June 10 | 0.21 ± 0.08 | 0.31 ± 0.07 |

In a further experiment, the sperm production of male turkeys was raised by administering the following four compounds:

Compound "A": D-Phe$^6$-GnRH
Compound "B": (Asp-α-anilide)$^6$,desGly$^{10}$-GnRH
Compound "C": D-Phe$^6$,desGly$^{10}$-GnRH ethylamide
Compound "D": (Asp-α-diethylamide)$^6$,desGly$^{10}$-GnRH ethylamide The sperm production was raised by all GnRH analogues tested, Compound "D" proved to be the most active (Table 5).

TABLE 5

Effect of gonadoliberin analogues on the sperm production of male turkeys

| Compound | at the beginning of the experiment | Sperm production ml/animal after | | | |
|---|---|---|---|---|---|
| | | 30 days | 60 days | 90 days | 120 days |
| "A" | 0.27 | 0.34 | 0.39 | — | — |
| n = 130 | ±0.04 | ±0.03 | ±0.04 | | |
| "B" | 0.18 | 0.21 | 0.28 | — | — |
| n = 150 | ±0.06 | ±0.02 | ±0.03 | | |
| "C" | 0.21 | 0.30 | 0.32 | 0.34 | 0.30 |
| n = 180 | ±0.03 | ±0.04 | ±0.02 | ±0.05 | ±0.03 |
| "D" | 0.20 | 0.23 | 0.33 | 0.36 | 0.34 |
| n = 200 | ±0.02 | ±0.02 | ±0.04 | ±0.03 | ±0.04 |
| Control | 0.19 | 0.19 | 0.20 | 0.21 | 0.20 |
| n = 200 | ±0.04 | ±0.05 | ±0.02 | ±0.03 | ±0.04 |

The results obtained in experiments carried out on a high number of various animals unambiguously support our observation of the fact that the sperm production of male turkeys is maintained by using LH-RH analogues at a high level for several months following a "latency period" which lasts for about 3 weeks.

EXAMPLE 2

Change of the sexual activity and of the blood plasma testosterone level of ganders on effect of a GnRH analogue Ganders kept under large-scale conditions and propagated in a natural way were treated with 0.5 μg/kg of D-Phe$^6$,desGly$^{10}$-GnRH ethylamide analogue every 2 days, altogether 3 times. Both the blood plasma testosterone level as well as the libido of the animals were significantly raised by the treatment. This manifested itself in the rise of the copulation activity (Table 6).

TABLE 6

Effect of treating with D-Phe$^6$, desGly$^{10}$—GnRH ethylamide analogue ganders copulating in early autumn on the blood plasma testosterone level and on the copulation activity (treatments: September 3, 10, 17 and 24)

| | Control (n = 10) | | Treated (n = 10) | |
|---|---|---|---|---|
| Sampling time | Testosterone pg*/ml | No. of daily copulations | Testosterone pg*/ml | No. of daily copulations |
| September 3 | 396 ± 123 | 8 | 378 ± 142 | 9 |
| September 10 | 408 ± 152 | 9 | 470 ± 133 | 7 |
| September 17 | 416 ± 163 | 8 | 879 ± 145 | 12 |
| September 24 | 327 ± 130 | 7 | 695 ± 125 | 13 |
| October 1 | 310 ± 89 | 7 | 390 ± 78 | 10 |

*pg = picogramm

The copulation activity of the treated animals exceeded that of the control ganders by 40 to 50% and was maintained at this high level for one additional month.

EXAMPLE 3

Increase in the sperm production of ganders

"Hungarian" and "Landes" ganders kept under natural conditions and divided to small groups were treated with 0.5 μg/kg of D-Phe$^6$,desGly$^{10}$-GnRH ethylamide analogue every 2 days, altogether 3 times. This treatment resulted in a sperm production increase lasting for about one month and a half (Table 7). In case of the "Hungarian" ganders the sperm volume was significantly increased and simultaneously the quality of the sperm was also improved, i.e. the number of the spermatozoa in unit sperm volume and the motility of them were raised whereas the number of the dead or deficinet spermatozoa was diminished.

TABLE 7

Effect of D-Phe$^6$, desGly$^{10}$—GnRH ethylamide on the sperm production of ganders kept under natural conditions and copulating in the spring (treatments: January 28, 30 and February 1)

| Sampling time | Sperm (ml) | | No. of spermatozoa 10$^6$/mm$^3$ | | Ratio of dead + deficient cells (%) | | Motility of the spermatozoa | |
|---|---|---|---|---|---|---|---|---|
| | Control | Treatment | Control | Treatment | Control | Treatment | Control | Treatment |
| | | | "Hungarian" | | | | | |
| January 15 | 0.18 | 0.19 | 2.3 | 2.1 | 16 | 19 | weak | weak |
| | ±0.06 | 0.06 | | | | | | |
| January 31 | 0.27 | 0.25 | 2.2 | 2.3 | 17 | 20 | medium | weak |
| | 0.08 | 0.05 | | | | | | |
| February 7 | 0.22 | 0.48 | 2.2 | 3.2 | 16 | 8 | medium | good |
| | 0.10 | 0.12 | | | | | | |
| February 14 | 0.30 | 0.56 | 1.9 | 3.0 | 12 | 10 | medium | good |
| | 0.16 | 0.20 | | | | | | |
| February 21 | 0.23 | 0.30 | 2.3 | 2.9 | 14 | 12 | good | good |
| | 0.10 | 0.12 | | | | | | |
| February 28 | 0.21 | 0.23 | 2.4 | 2.9 | 16 | 14 | medium | good |
| | 0.08 | 0.09 | | | | | | |
| March 7 | 0.28 | 0.44 | 2.6 | 3.1 | 19 | 17 | good | good |
| | 0.11 | 0.19 | | | | | | |
| March 12 | 0.29 | 0.33 | 2.6 | 3.0 | 17 | 14 | medium | good |
| | 0.09 | 0.12 | | | | | | |
| | | | "Landes" | | | | | |

TABLE 7-continued

Effect of D-Phe$^6$, desGly$^{10}$—GnRH ethylamide on the sperm production of ganders kept under natural conditions and copulating in the spring (treatments: January 28, 30 and February 1)

| Sampling time | Sperm (ml) Control | Sperm (ml) Treatment | No. of spermatozoa 10$^6$/mm$^3$ Control | No. of spermatozoa 10$^6$/mm$^3$ Treatment | Ratio of dead + deficient cells (%) Control | Ratio of dead + deficient cells (%) Treatment | Motility of the spermatozoa Control | Motility of the spermatozoa Treatment |
|---|---|---|---|---|---|---|---|---|
| January 15 | 0.16 | 0.19 | 1.8 | 1.9 | 24 | 23 | weak | weak |
|  | 0.07 | 0.05 |  |  |  |  |  |  |
| January 31 | 0.22 | 0.43 | 1.9 | 2.0 | 23 | 23 | weak | medium |
|  | 0.10 | 0.16 |  |  |  |  |  |  |
| February 7 | 0.20 | 0.32 | 1.9 | 2.2 | 23 | 19 | medium | medium |
|  | 0.07 | 0.10 |  |  |  |  |  |  |
| February 14 | 0.23 | 0.45 | 1.9 | 2.0 | 22 | 16 | medium | good |
|  | 0.12 | 0.17 |  |  |  |  |  |  |
| February 21 | 0.27 | 0.38 | 1.7 | 2.0 | 18 | 19 | medium | medium |
|  | 0.12 | 0.13 |  |  |  |  |  |  |
| February 28 | 0.30 | 0.35 | 1.8 | 2.2 | 19 | 17 | weak | medium |
|  | 0.14 | 0.11 |  |  |  |  |  |  |
| March 7 | 0.20 | 0.18 | 1.9 | 1.9 | 17 | 20 | medium | good |
|  | 0.08 | 0.06 |  |  |  |  |  |  |
| March 12 | 0.24 | 0.20 | 1.8 | 1.8 | 20 | 19 | medium | medium |
|  | 0.09 | 0.12 |  |  |  |  |  |  |

EXAMPLE 4

Enhancement of the sexual activity of male parrots 0.1 μg/kg of (Asp-α-diethylamide)$^6$,desGly$^{10}$-GnRH ethylamide analogue was injected to sexually inactive male arara parrots kept under natural conditions every 3 days, altogether 3 times. The penis of the animals was significantly enlarged on the effect of this treatment. The animals showed a characteristic ethological change (wooing) and the increase in their sexual activity manifested itself also in repeated copulations.

EXAMPLE 3

Enhancement of the sperm production of male rabbits by using a GnRH analogue

In this experiment male angora rabbits showing a low libido were used from which no sperm could be obtained. The motility of the cells in their sperm was lower than 75%; thus, these animals could not be used for propagating. Of these animals 234 were treated with 3 μg of D-Phe$^6$,desGly$^{10}$-GnRH ethylamide analogue every 2 days, altogether 3 times. While the sexual activity of the control animals was substantially unaltered, the following observations were made on the treated animals within a period lasting 4 weeks after the treatment: the libido of the animals was significantly increased; their sperm production reached 80% (weighed in ml) of the average weight of sperm obtained from good males useful for breeding; further on, the motility characteristic of the insemination ability of spermatozoa exceeded in average by 10% the mean value (76%) of the sperm obtained from good males. These effects could be observed for several weeks; thus, the amount of the sperm usable for artificial insemination increased to its 2.5-fold value.

EXAMPLE 6

Enhancement of the sexual activity of a bull

A 2-year old bull of 1010 kg weight, of breeding condition and correspondingly having a good muscular system, good leg construction and a definitely male sexual character was set to breeding in 1985. On October 16 and 23 as well as on Nov. 1, 1985 test coverings were carried out on a rutting female cattle and on a phantom bull. The animal has not sprung in any case and did not show any interest either to the female or to the male animal. Diagnosis stated by the veterinarian specialist: importentia coeundi.

The bull was treated on November 29 as well as on Dec. 2 and 4, 1986 altogether 3 times with 300 μg each of D-Phe$^6$-GnRH analogue. On Dec. 6, 1985 the bull covered two times a rutting cow and this action was repeated on Jan. 7, 1986. On Jan. 21, 1986 the bull sprung onto a cow being after rutting. The sexual potency of the animal was unobjectionable even after 5 weeks following the treatment.

What we claim is:

1. A process for increasing the sexual activity of birds and useful domestic mammals and for preparing spermatozoa suitable to their propagation, which comprises treating sexually mature male birds or useful domestic mammals at least twice and at most four times, with 0.1 to 5 μg/kg of body weight of a GnRH analogue of the formula, $$\text{Glp-His-Trp-Ser-Tyr-X}_1\text{-Leu-Arg-Pro-X}_4$$

wherein $X_1$ stands for a glycyl group, a natural or synthetic aminoacid or aminoacid derivative of D configuration, or an -Asp-Q group of L configuration, wherein Q is attached to the α-carbonyl moiety of the aspartyl group and represents a $C_{1-5}$ alkylamide, an arylamide, a $C_{1-4}$ alkoxy or a benzyloxy group; and $X_4$ stands for a glycylamide or a $C_{1-4}$ alkylamide group, while keeping a pause of at least 30 hours and at most 72 hours between the consecutive treatments, whereby a long-term increase in sexual activity and sperm production suitable for propagation is obtained.

2. The process of claim 1, in which the animals are treated three times with the GnRH analogue.

3. The process of claim 1, in which the animals are treated with an amount of 0.5 to 1.0 μg/kg of body weight of the GnRH analogue.

4. The process of claim 1, in which a pause of 36 to 42 hours is kept between the consecutive treatments.

5. The process of claim 2 in which the animals are treated with an amount of 0.5 to 1.0 μg/kg of body weight of the GnRH analogue.

6. The process of claim 2 in which a pause of 36 to 42 hours is kept between the consecutive treatments.

7. The process of claim 3 in which a pause of 36 to 42 hours is kept between the consecutive treatments.